United States Patent
Jepsen et al.

(10) Patent No.: US 6,679,105 B1
(45) Date of Patent: Jan. 20, 2004

(54) OSCILLATORY EROSION AND TRANSPORT FLUME WITH SUPERIMPOSED UNIDIRECTIONAL FLOW

(75) Inventors: Richard A. Jepsen, Albuquerque, NM (US); Jesse D. Roberts, Carlsbad, NM (US)

(73) Assignee: Sandia Corporation, Albuquerque, NM (US)

( * ) Notice: Subject to any disclaimer, the term of this patent is extended or adjusted under 35 U.S.C. 154(b) by 0 days.

(21) Appl. No.: 10/376,193

(22) Filed: Feb. 27, 2003

Related U.S. Application Data

(63) Continuation-in-part of application No. 09/955,640, filed on Sep. 19, 2001, now Pat. No. 6,494,084.
(60) Provisional application No. 60/385,055, filed on May 29, 2002.

(51) Int. Cl.[7] ............................................... G01N 17/00
(52) U.S. Cl. .......................................................... 73/86
(58) Field of Search ..................... 73/86, 841; 137/571, 137/576

(56) References Cited

U.S. PATENT DOCUMENTS

| | | | |
|---|---|---|---|
| 1,826,112 A | * | 10/1931 | Wilson ........................... 137/8 |
| 6,260,409 B1 | | 7/2001 | Briaud et al. |
| 6,494,084 B1 | | 12/2002 | Roberts et al. |

OTHER PUBLICATIONS

U.S. patent application Ser. No. 60/385,055, Jepsen et al., filed May 29, 2002.

*Measurements of Erosion of Undisturbed Bottom Sediments with Depth*, J. McNeil, C. Taylor, and W. Lick, Journal of Hydraulic Engineering, Jun., 1996.

*Effects of Bulk Density on Sediment Erosion Rates*, R. Jepsen, J. Roberts, and W. Lick, Journal of Water, Air and Soil Pollution 99, pp. 21–31, Jun., 1997.

*Development of Flume with Oscillatory Flow Superimposed over a Unidirectional Flow*, Sandia National Laboratories fact sheet, R. Jepsen and J. Roberts, http://www.nwer.sandia.gov/wlp/factsheets/oscflow,pdf, Jul. 1, 2001.

*The Seawolf Flume: Sediment Erosion Actuated by Wave Oscillations and Linear Flow*, Richard Jepsen, Jesse Roberts, Joseph Z. Gailani, and S. Jarrell Smith, Sandia National Laboratories technical report SAND2002–0100, Jan., 2002.

* cited by examiner

Primary Examiner—Robert Raevis
(74) Attorney, Agent, or Firm—Robert D. Watson

(57) ABSTRACT

A method and apparatus for measuring erosion rates of sediments and at high shear stresses due to complex wave action with, or without, a superimposed unidirectional current. Water is forced in a channel past an exposed sediment core sample, which erodes sediments when a critical shear stress has been exceeded. The height of the core sample is adjusted during testing so that the sediment surface remains level with the bottom of the channel as the sediments erode. Complex wave action is simulated by driving tandom piston/cylinder mechanisms with computer-controlled stepper motors. Unidirectional flow, forced by a head difference between two open tanks attached to each end of the channel, may be superimposed on to the complex wave action. Sediment traps may be used to collect bedload sediments. The total erosion rate equals the change in height of the sediment core sample divided by a fixed period of time.

8 Claims, 7 Drawing Sheets

OSCILLATORY EROSION AND TRANSPORT FLUME WITH SUPERIMPOSED UNIDIRECTIONAL FLOW

CROSS-REFERENCE TO RELATED APPLICATIONS

This application is a continuation-in-part of application Ser. No. 09/955,640, filed Sep. 19, 2001 (now U.S. Pat. No. 6,494,084), which is incorporated by reference. This application claims the benefit of U.S. Provisional Application No. 60/385,055, filed May 29, 2002, which is incorporated by reference.

FEDERALLY SPONSORED RESEARCH

The United States Government has rights in this invention pursuant to Department of Energy Contract No. DE-AC04-94AL85000 with Sandia Corporation.

BACKGROUND OF THE INVENTION

The present invention relates generally to a method and apparatus for measuring aqueous erosion and transport from a sediment core sample. More specifically, the present invention relates to an adjustable shear stress erosion and transport flume having a variable-depth sediment core sample with the capability to simulate complex wave action with, or without, a superimposed unidirectional flow.

Many contaminants are sorbed to sedimentary particles and are buried at depths of up to several meters in the bottom sediments of rivers, lakes, estuaries, navigation channels, beaches and near-shore areas of the oceans. An important question is whether these buried sediments (and associated contaminants) can be exposed and transported during large floods and storms, releases from dams, etc., either with or without oscillatory wave action. In order to answer this question, knowledge of the erosion and transport properties of sediments at high shear stresses (up to and exceeding 10 Pa) and with depth through the sediment layer (up to and exceeding one meter) is needed.

To characterize the movement of sediments in aquatic systems one must not only have an understanding of the bulk erosion rates of sediments, but also be able to distinguish between two primary modes of sediment transport, i.e., suspended transport and bedload transport. As shown in FIG. 1, suspended transport of a sediment grain or particle in flowing water occurs when the vertical component of the turbulent flow velocity is approximately equal to or greater than the settling (i.e., falling) speed of the grain. Unsuspended transport, also known as bedload transport, includes a variety of transport mechanisms, such as saltation, rolling, sliding, and tumbling. Saltation occurs when a particle momentarily leaves the bed and rises no higher than a few grain diameters. Rolling, sliding, and tumbling are additional processes wherein particles are transported along the bed primarily by the horizontal force of the overlying flow of water. In bedload transport, the particles receive no significant upward impulses other than those due to successive contacts between the solid and the bed; the fluid impulses on the grains being essentially horizontal. Saltation transport is generally included in the category of bedload transport since saltation is restricted to only a few grain diameters in height above the bed.

Erosion and transport of sediments in rivers and streambeds, along ocean beaches, harbors, navigation channels and waterways, and around bridge support structures, is a complex process that depends on many variables. Sediments may erode particle-by-particle (e.g., sand and gravel), or may erode as aggregates or chunks, especially if the particles are fine-grained and cohesive (e.g., clay or silt). The aggregates/chunks can vary in size from microns to centimeters; generally do not re-suspend; and are made from very fine-grained particles that likely would re-suspend if disaggregated.

Sediments may also be contaminated with chemical, biological, or industrial contaminants, which can affect the degree of cohesiveness. Erosion and transport rates can also depend on grain size, shape, density, degree of cohesiveness, chemistry, organic content, and gas content. As shown in FIG. 2, aggregated (cohesive) particles eroded from the bed at an upstream position, $X_1$, can de-aggregate at a downstream position, $X_2$, due to subsequent impacts and collisions with the channel bottom and/or other aggregates and particles (e.g., during saltation transport).

Erosion rates and transport modes also depend on the shear stress applied across the sediment's surface by velocity of the flowing liquid (e.g., water). Typically, a threshold exists where no appreciable erosion occurs below a critical shear stress. The critical shear stress for erosion may depend on whether or not the flow is unidirectional, oscillatory, non-uniform/irregular, or combinations of these.

Accurate prediction of erosion rates (bulk/total, suspended, and bedload) and subsequent transport and re-deposition for each mode of transport (suspended or bedload) is complicated by a lack of understanding of the cohesive forces that bind together fine-grained sediments (especially for contaminated sediments). Therefore, a need exists for an apparatus that can accurately measure the individual contributions to the total erosion rate of sediments from suspended and bedload erosion processes, whether in the laboratory or in the field, including oscillatory flow.

A previous apparatus for measuring bulk erosion of sediments, called a "SEDflume", is described in "*Measurements of Erosion of Undisturbed Bottom Sediments with Depth*", J. McNeil, C. Taylor, and W. Lick, Journal of Hydraulic Engineering, June, 1996. A similar device is described in U.S. Pat. Ser. 6,260,409 to Briaud, et al., "Apparatus and Method for Prediction of Scour Related information in Soils". However, these devices can only measure the total (i.e., bulk) erosion rate of a sediment core sample; they cannot independently measure the separate contributions from suspended and bedload erosion sources.

U.S. Pat. No. 6,494,084, "Adjustable Shear Stress Erosion and Transport Flume", to Roberts and Jepsen, which is incorporated by reference, describes an improvement to the SEDflume device. Certain embodiments of this invention comprise a SEDflume type device with one or more traps (e.g., capture basins) located downstream of the sediment core sample. The bedload sediments (i.e., particles and aggregates) transported in the flow stream are gravitationally separated and captured in the downstream traps. The use of downstream traps allows measurement of the individual contributions of the total erosion rate from sediments suspended in the flow stream; and from bedload sediments transported along the floor (i.e., bed) of the channel.

However, none of the devices described above have means for simulating complex wave action (including oscillating flow) either alone, or in combination with, a superimposed unidirectional flow.

Hence, a need still exists for a device that can measure sediment transport properties of cohesive and non-cohesive sediments with depth and at high shear stresses due to complex wave action with, or without, a superimposed unidirectional current. Against this background, the present invention was developed.

SUMMARY OF THE INVENTION

The present invention relates to a method and apparatus for measuring erosion rates of sediments and at high shear stresses due to complex wave action with, or without, a superimposed unidirectional current. Water is forced in a channel past an exposed sediment core sample, which erodes sediments when a critical shear stress has been exceeded. The height of the core sample is adjusted during testing so that the sediment surface remains level with the bottom of the channel as the sediments erode. Complex wave action is simulated by driving tandom piston/cylinder mechanisms with computer-controlled stepper motors. Unidirectional flow, forced by a head difference between two open tanks attached to each end of the channel, may be superimposed on to the complex wave action. Sediment traps may be used to collect bedload sediments. The total erosion rate equals the change in height of the sediment core sample divided by a fixed period of time.

Sandia National Laboratories (SNL) has designed, constructed, and tested a high shear stress flume that can superimpose an complex wave action upon a unidirectional current. This apparatus is named the Sediment Erosion Actuated by Wave Oscillations and Linear Flow (SEAWOLF) flume. The SEAWOLF flume can be housed in a self-contained, mobile trailer and used on-site in research and mission support investigations of combined unidirectional current and wave induced erosion of in-situ contaminated sediments, dredged material mixtures composed of cohesive and non-cohesive sediments, or other sediments.

Results from hydrodynamic modeling of the SEAWOLF flume indicate oscillatory flow regimes in the SEAWOLF flume induce shear stresses up to 10 Pa. The addition of unidirectional flow can induce shear stresses greater than 12 Pa. Erosion experiments were performed using the SEAWOLF apparatus under a range of unidirectional and oscillatory flow combinations. These experiments verified model predictions that the undeveloped oscillatory flow shear stresses are much greater than those generated by fully developed, unidirectional flow. Effective shear stresses were determined from erosion tests with known sediment samples, making SEAWOLF a useful tool for predictive modeling.

The SEAWOLF apparatus may also be used to measure the critical shear stress necessary to initiate erosion.

The SEAWOLF flume may incorporate one or more upstream or downstream sediment traps. Eroded bedload sediments are transported downstream are gravitationally separated from the flow stream into one or more sediment trap (i.e., capture basins). After a known period of time, the bedload sediments (both particles and aggregates) that were captured in the trap(s) are weighed and compared to the total mass of sediment eroded (as measured by the change in height of the core sample), and may also be compared to the concentration of sediments suspended in the flow stream.

The SEAWOLF flume is described in *Development of Flume with Oscillatory Flow Superimposed over a unidirectional Flow*, Sandia National Laboratories, http://www.nwer.sandia.gov/wlp/factsheets/oscflow.pdf, Jul. 1, 2001, which is incorporated herein by reference.

The SEAWOLF flume is also described in *The SEAWOLF Flume: Sediment Erosion Actuated by Wave Oscillations and Linear Flow*, by Richard Jepsen, Jesse Roberts, Joseph Z. Gailani, and S., Jarrell Smith, Sandia National Laboratories technical report SAND2002-0100, January, 2002, which is incorporated herein by reference.

BRIEF DESCRIPTION OF THE DRAWINGS

The accompanying drawings, which are incorporated in and form part of the specification, illustrate various examples of the present invention and, together with the detailed description, serve to explain the principles of the invention.

DETAILED DESCRIPTION OF THE INVENTION

Herein, we define erosion to include scouring. We define the bulk or total erosion rate to equal the sum of the suspended erosion rate and the bedload erosion rate. We define sediments to include grains, particles, particulates, and aggregates (or chunks) of grains or particles that are adhered together with cohesive forces. We define bedload transport processes to include saltation, rolling, sliding, and tumbling modes, and combinations thereof. The phrases "erosion flume" and "erosion apparatus" and "erosion device" are used interchangably herein. The words "oscillatory" and "oscillating" are meant to broadly include not only simple sinusoidal waves that repeat with a regular period, but also complex, non-sinusoidal waveforms that may or may not be repetitive. The words "unidirectional flow" means flow in a single direction at a constant flow rate with respect to time. The words "non-uniform flow" means that the flow is not flowing at a constant rate with respect to time, but, rather, the flow rate is changing with respect to time.

Figure 1:
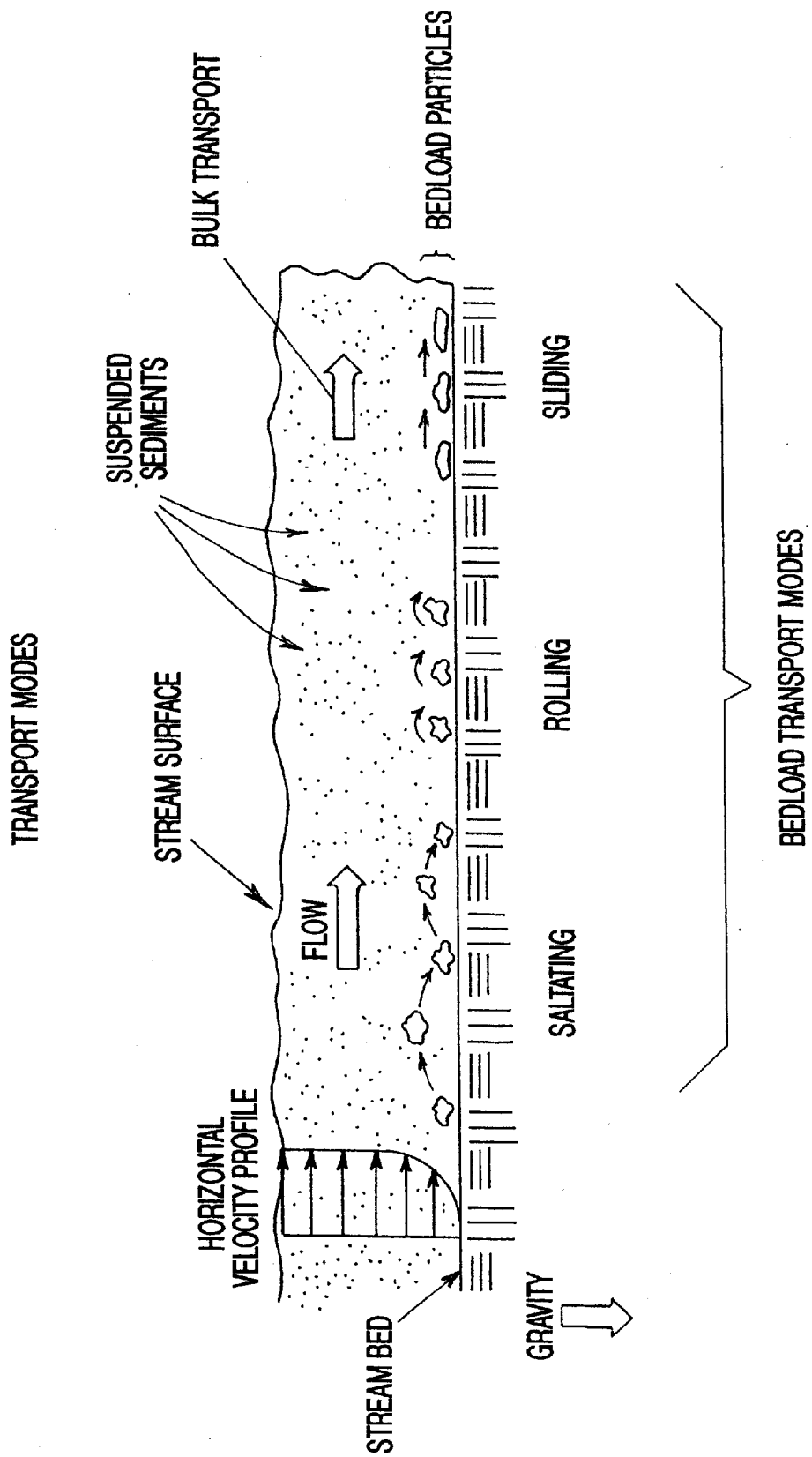
FIG. 1 shows a schematic side view of a streambed with flowing water causing erosion of sediments, illustrating the difference between suspended and bedload transport of eroded sediments.
Figure 2:
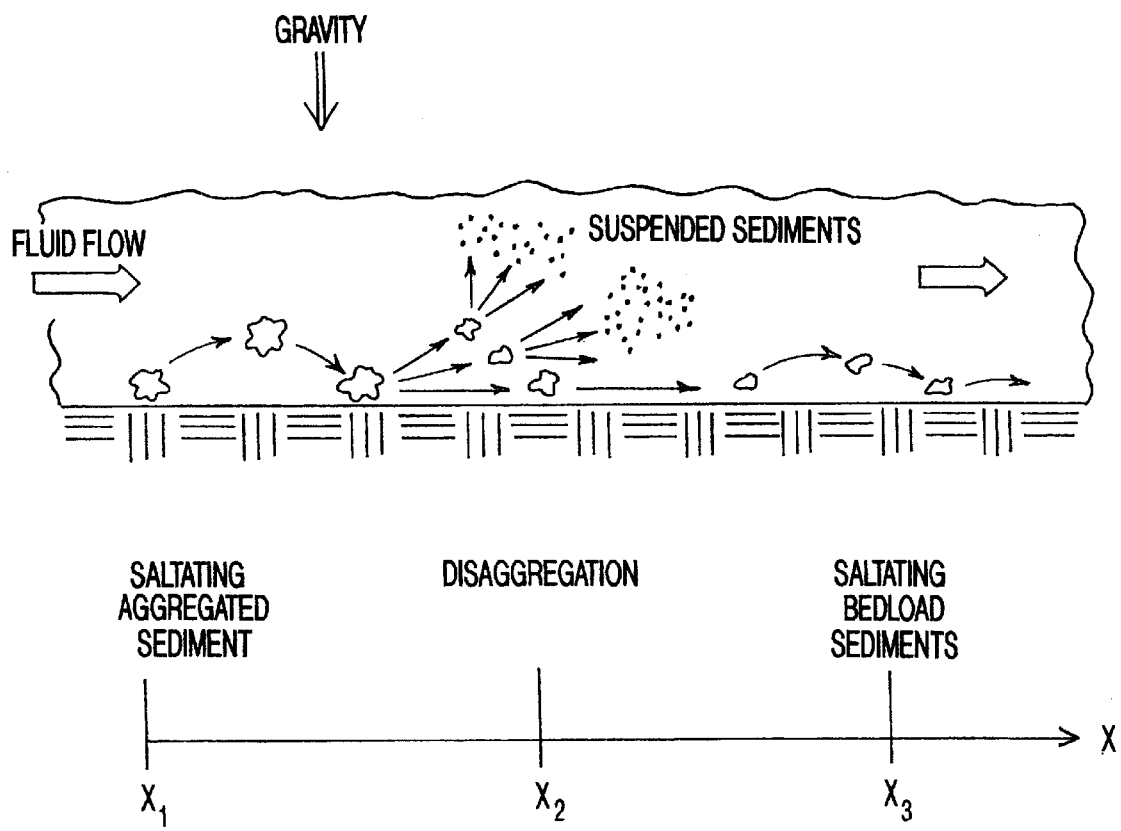
FIG. 2 shows a schematic side view of a stream bed with flowing water eroding sediments, illustrating how a saltating, aggregated sediment particle that was eroded at position $X_1$ can disaggregate into smaller particles at a downstream location, $X_2$; wherein the smaller particles can subsequently be transported either as suspended sediments or as bedload sediments.
Figure 3:
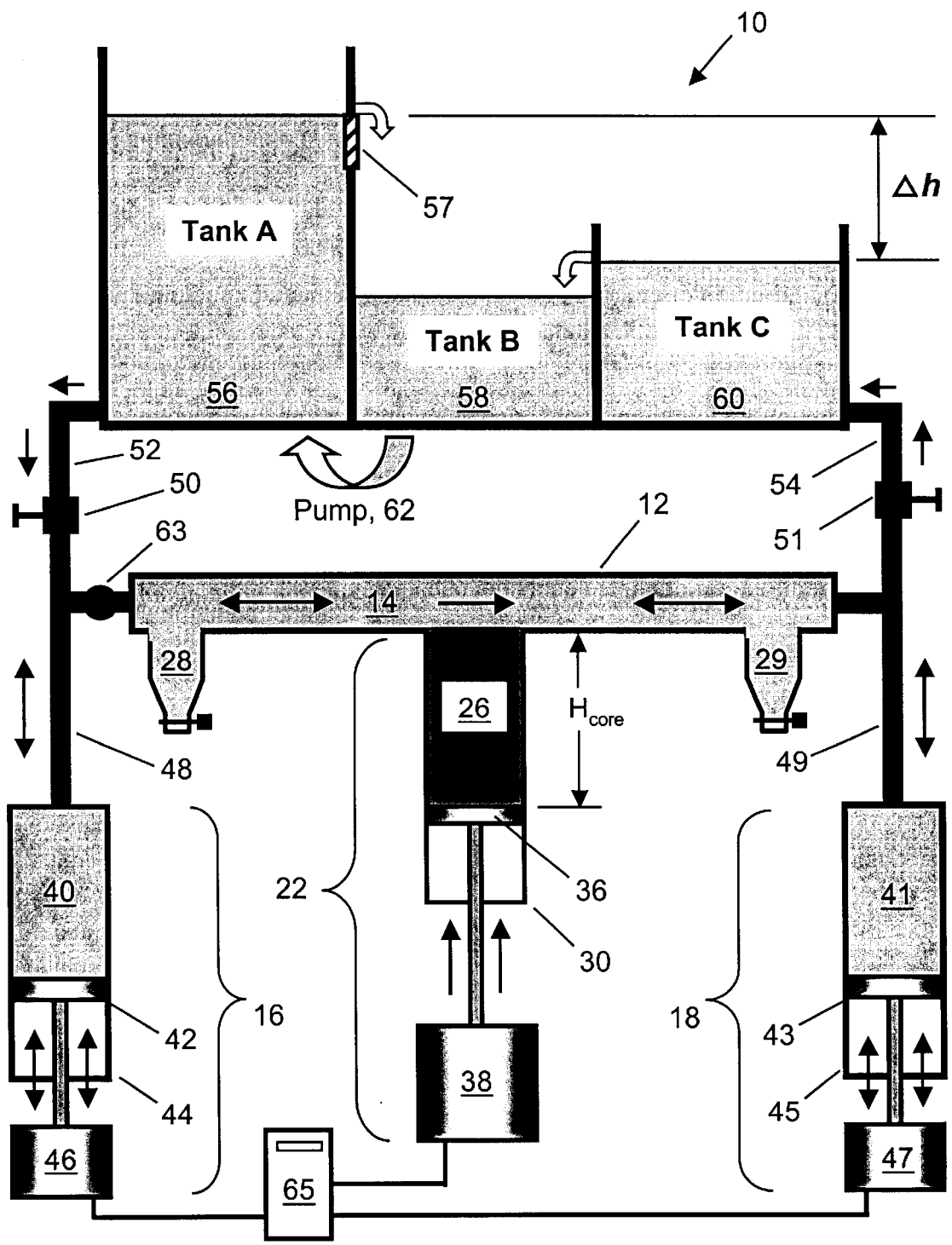
FIG. 3 shows a schematic side view of a cross-section of an example of a SEAWOLF erosion flume/apparatus, according the present invention.

FIG. 3 shows a schematic side view of a cross-section of an example of a SEAWOLF erosion flume/apparatus, according the present invention. Flume 10 comprises flow channel 12 for conveying a stream of flowing fluid 14, and erosion means 22 attached to an opening in the bottom of channel 12 for exposing one end of a sediment core sample 26 to shear stresses applied by fluid 14 flowing horizontally across the surface of core sample 26. The scouring/shearing action of flow stream 14 erodes sediments from core sample 26 and introduces them into flow stream 14. These eroded sediments generally include a mixture of bedload sediments and suspended sediments, both of which are transported along channel 12.

An optional pair of sediment traps 28, 29 (i.e., capture basins, gravitational traps) may be located either upstream or downstream (or both) of core sample 26 to catch bedload sediments that fall into the traps by gravity. The use of sediment traps 28, 29 can help to insure that the test section does not experience sediment-laden water from previously eroded material. Also, a measurement of the bedload erosion rate may be made by weighing the amount of material collected in the trap(s) during a fixed period of time. Flow channel 12 may be about two meters long, and may be made of clear polycarbonate plastic, with a circular, square or rectangular, closed cross-section. The height of channel 14 may be about 2 cm.

Core sample erosion means 22 may comprise a piston/cylinder mechanism for pushing/urging sediment core sample 26 into flow stream 14. The core is gradually moved upward by the operator (either manually or controlled by computer 65) at a rate such that the sediment surface (i.e., the sediment/water interface) remains level (i.e., flush) with the bottom of (or slightly protruding from) the flume channel during testing. Core sample 26 may be extracted directly from a field site, or may be artificially created in the laboratory. The total erosion rate is defined as the amount of upward movement of the core sample 26 divided by a known period of time. Typically, less than about 2 cm of core sample sediment is eroded during an erosion test. The height (i.e., length) of core sample 26 ($H_{core}$) is typically about 40–80 cm and therefore permits analysis of sediment erosion as a function of depth below the initial sediment/water interface.

Referring still to FIG. 3, the net unidirectional flow (i.e., current) in the test section (i.e., the section of channel 14 close to and including core sample 26) is controlled by the head difference $\Delta h$ between tank A (56) and Tank C (60). Water is pumped from Tank B (58) to Tank A (56) by pump 62 to maintain the desired head in Tank A (56), which is greater than the head in Tank C (60). An adjustable-height gate 57 may be used to set the upper level of Tank A (56). This head difference, $\Delta h$, drives the unidirectional flow. To adjust the unidirectional flow rate, $\Delta h$ can be changed between each erosion test by raising or lowering gate 57. Both Tank A (56) and Tank C (60) overflow into the central reservoir, Tank B (58), which allows a constant $\Delta h$ to be maintained during testing. A net current of water flows in a closed, recirculating loop from Tank A (56), through pipe 52, valve 50, and flow meter 63, to the upstream entrance of channel 14, through channel 14, from channel 14, through pipe 54 and valve 51 to Tank C (60), where it spills into Tank B (58), and then is pumped into Tank A (56) by pump 62. In one embodiment, unidirectional flow rates may range between 0 and 35 gpm (gallons per minute). This amount of unidirectional flow can create shear stresses in the range of 0.1 to 3 Pa. Pipes 52 and 54 may be 2" diameter plastic (e.g., PVC) pipe.

The head difference, $\Delta h$, between Tanks A (56) and C (60) drives the velocity of the unidirectional flow in channel 12. The unidirectional flow velocity may be calculated from the Bernoulli equation:

$$\frac{P_A}{\rho} - \frac{v_c^2}{2} + g\Delta h = \frac{P_C}{\rho} + h_l, \tag{1}$$

g=gravity (m/s$^2$),
$h_l$=head losses (inlet, exit, channel, 90° pipe bends) (m$^2$/s$^2$),
$\Delta h$=head difference (m),
$P_{A,C}$=Pressure in Tanks A and C (N/m$^2$).

The pressures, $P_A$ and $P_C$, are equal because both tanks are open to the atmosphere. Solving for $v_c$ in equation (1) yields, $$v_c = \sqrt{2g\Delta h - 2h_l} \tag{2}$$

Head loss in the flume is estimated by accounting for flow rate, pipe diameter, pipe length, and pipe bends. For example, head difference of 0.45 m results in an approximate head loss of 4.0 m$^2$/s$^2$ and current velocity of 1 m/s when valves 50, 51 to the tank are fully open. Partially closing valves 50 and/or 51 will increase the head loss. Valve adjustment offers fine control of the unidirectional flow rates. Although it is possible to calculate the head loss, it is not necessary for regular operation of the flume. Flow meter 63 provides all relevant flow information and this calculation was performed only for design purposes.

Complex wave action (including simple oscillatory flow) inside of channel 12 may be attached to the entrance (left) and exit (right) ends of channel 12, respectively. Computer 65 controls the operations of stepper motors 46, 47, which drive pistons 42, 43 (using a ball-screw arrangement) inside of cylinders 44, 45, that push or pull on fluid volumes 40, 41. In this sense, tandom piston/cylinder mechanisms 16, 18 act as positive displacement pumps.

Tandom piston/cylinder mechanisms 16, 18 may be operated completely independently from each other by computer 65. Each piston/cylinder mechanism may have different waveforms, stroke displacements, frequencies/periods, velocities, timings, phase angles, etc. One or more digital representations of one or more complex waveforms (e.g., piston displacement versus time, net flow rate versus time, etc.) may be stored in computer 65 and used to independently control the operation of each stepper motor to drive each piston displacement according to the digital representation of a complex waveform (i.e., digitized shape). Both oscillatory and non-oscillatory flow may be generated. For oscillatory flow, tandom piston/cylinder mechanisms 16, 18 act may be operated as a coordinated pair with identical stroke displacement and piston velocities, but timed 180 degrees out-of-phase from each other, so that one piston is pushing while the other is pulling (and visa-versa). A single waveform may have any shape that can be digitized and digitally generated by the computer-controlled stepper motors 46, 47, including simple shapes such as: square, impulse, triangular, ramped, trapezoidal, exponential, or sinusoidal. The waveforms may be repeated over time in a regular fashion (as simple oscillatory flow), or non-uniformly or randomly with respect to time. A trapezoidal wave shape may be used to closely approximate a half-sine wave shape. Linear (i.e., unidirectional) flow may be superimposed on any of the wave shapes described previously in this paragraph.

Referring still to FIG. 3, valves 50 and 51 (e.g., ball valves) may be located in-between the left end of channel 12 and tank A (56), and in-between the right end of channel 12 and Tank C (60), respectively, and may be used to control both the unidirectional flow rate and the backflow into the tanks from the oscillatory flow. Within the test section, unidirectional flow rates can range between 0 and 35 gpm and the oscillatory peak rates range between 0 and 39 gpm. Valves 50 and 51 connecting the channel to the tanks may be unequally adjusted to manipulate backflow from the piston (s) strokes. When valves 50 and 51 are not closed, water can spill over (i.e., backflow) into Tanks A, B, and C. This arrangement permits tandom piston/cylinder mechanisms 16, 18 to generate complex wave shapes that may force a net flow of water into (or out of) Tanks A, B, and C (for example, if both piston/cylinder mechanisms 16, 18 are pushing (or pulling) at the same time. However, if valves 50 and 51 are closed, then the tandom piston/cylinder mechanisms 16, 18 should be operated in a synchornized, push/pull manner with each piston displacing the same volume of water, since there is no compliance in the schematic example of a system illustrated in FIG. 3.

These adjustments permit a SEAWOLF erosion device to simulate a wide range of complex wave conditions and shear stresses at the sediment water interface. In one embodiment, the SEAWOLF apparatus permits the operator to conduct erosion rate experiments for shear stresses ranging from 0.1 Pa up to 10 Pa for pure oscillatory flow; and over 12 Pa for combined oscillatory and unidirectional flow. Flowmeter 63 may be used to measure the instantaneous flow rate (e.g., gpm) through channel 14. Flowmeter 63 may be a DeltaForce™ magnetic flow meter, or other suitable meter.

Referring still to FIG. 3, flow channel 12 may be oriented substantially horizontally with respect to gravity. Alternatively, flow channel 12 may be oriented at a pitched angle relative to horizontal (not shown), which could be used with free-flowing, gravity-driven flow of fluid 14, e.g., from a dam spillway or culvert pipe. In these cases, channel may be open (i.e. open to the atmosphere). Typically, flow channel 12 is oriented such that the direction of fluid flow is horizontal and the long axis of core sample 26 is vertical. However, flow channel 12 may be tilted or rotated about its longitudinal axis (i.e., the direction of fluid flow) to a non-vertical orientation in order to simulate flow on the side of a riverbank. Apparatus 10 can be rigidly supported by well-known structural support means or structural framework (not shown). Apparatus 10 can be housed in a laboratory room, or optionally provided as a mobile system, such as in a truck or mobile trailer, that can be moved to a test site in the field.

Channel means 12 may be an open or closed (i.e., internal) channel. If open, channel 12 may be a three-sided, "U"-shaped open channel with a rectangular or square cross-section, or a one-sided shape having a curved cross-section. If closed, channel 12 may be pipe, tube, or flume having a circular, oval, elliptical, square, or rectangular cross-section. Channel 12 may be made of an optically transparent material, such as glass, clear polycarbonate or clear acrylic plastic, to permit viewing of the eroding surface and flow conditions during operation. Channel 12 may comprise a single-piece pipe or tube, such as made by extrusion or casting. Alternatively, channel 12 may comprise an assembly of plates that can be held together in a fluid-tight assembly by bolts used to compress gaskets, O-ring seals, or coil-spring seals at the mating surfaces. Flow stream 14 contained inside of channel 12 can flow essentially at atmospheric pressure, or at elevated pressures by pressurizing channel 12 above atmospheric pressure to simulate the pressure conditions at the bottom of a lake, river, or ocean, etc. Channel 12 may have a rectangular cross-section, with a channel height, $H_{channel}$, from 2–5 cm. Alternatively, $H_{channel}$ may be approximately 5 cm. Alternatively, $H_{channel}$ may be equal to or greater than approximately 2 cm. Alternatively, the height of channel 12 may be chosen to equal a substantial portion of the free stream's boundary layer thickness (e.g., 90%). The width of channel 12 may be approximately 10 cm. The width/height ratio may be 2:1 or greater. A closed channel configuration for channel 12 may be used in conjunction with high flow rates to achieve high shear stresses up to and exceeding 10 $N/m^2$, applied to the exposed surface sediment core sample 26.

Fluid 14 may comprise a multi-phase mixture of a liquid (e.g., water) and eroded solid sediments (suspended, bedload, or both). Alternatively, or additionally, fluid 14 may comprise externally added particles (sand, pebbles, sediments, leaves, sticks, gravel, etc.). Fluid 14 may comprise any liquid phase material, such as water, seawater, river water, contaminated water, oil, gasoline, etc. We use the term "water" interchangeably with "any liquid phase material" in this specification, since the most common applications primarily use water. Likewise, we use the phrases "fluid 14", "flow stream 14", "unidirectional flow", "net flow", and "current" interchangeably herein.

The shape of channel 12, as illustrated in FIG. 3, is shown as a straight section. However, channel 12 could also be curved in any manner necessary to simulate unusual flow conditions and/or hydrodynamic effects. For example, channel 12 may be curved in a way to simulate the complex multi-dimensional flow field of water around a bridge support post, pier, or piling in a river. A curved channel 12 may be used to artificially create a locally high pressure on the surface of sediment core sample 26 due to radial acceleration of fluid 14 in the curved channel geometry, potentially affecting the measured erosion rates for sediment core samples containing entrained gases (e.g., methane).

Referring still to FIG. 3, core sample erosion means 22 may comprise a mechanism for pushing up sediment core sample 26 into flow stream 14. Erosion means 22 may comprise a coring tube 30, which may be attached to the bottom of channel 12 with a removable bolt and gasket arrangement, or other type of removable, water-tight connection. Coring tube 30 holds and supports sediment core sample 26 while it is being pushed up (i.e., extruded) and urged (i.e., displaced) into flow stream 14 through an opening in the bottom of channel 12. In this sense, sediment core sample 26 has a "variable depth".

The term "variable depth" relates to at least three different aspects of the present invention. Firstly, as sample 26 erodes during erosion testing, its length naturally becomes shorter (i.e., the length varies over time). Secondly, the initial length (i.e. the starting length) of sediment core sample 26 does not need to be the same from test to test. It could start out, for example, as 10 cm long in one test, and then another sample could be installed for a second test that starts out with a 20 cm length (so long as it fits within the overall length of coring tube 30). Additionally, the overall length of coring tube 30 may be extended by adding extension tubes (not shown). Thirdly, the term "variable length" also refers to the possibility that sediment core sample 26 may not be homogenous throughout its depth, but, rather, may comprise a non-homogenous arrangement of multiple sediment layers that may vary through the depth of the sample (e.g., from sand to clay to sand plus pebbles, and so on), as might be found in a real sample taken from the field.

Coring tube 30 may have a circular, square, or rectangular cross section, and may be made of steel, or a clear glass or plastic material (i.e., for visualizing the sediment core sample 26). If cylindrically-shaped, the diameter of coring tube 30 may be approximately 10 cm, and the vertical length (i.e., height) may be approximately 1 meter long. The vertical height of tube 30 can be made as long as necessary by attaching extension tube segments (not shown), to accommodate very tall core samples (e.g., up to and exceeding 1 meter). This adjustable feature may be useful, for example, for studying the erosion of contaminants sorbed to sedimentary particles buried at depths of up to several meters in the bottom sediments of rivers, lakes, estuaries, and near-shore areas of the oceans.

Erosion means 22 may comprise a piston 36 disposed inside of coring tube 30, which pushes on the bottom of core sediment sample 26. Piston 36 is driven up or down by motorized drive 38 (e.g., worm gear, scissor-jack drive, stepper motor, hydraulic piston, pneumatic piston, linear motor, etc.). With appropriate gearing, a vertical position accuracy of +/−0.25 mm may be achieved. Erosion means 22 may further comprise displacement-measuring means (not shown) for measuring changes in $H_{core}$ or for measuring the displacement of piston 36 (such as a calibrated ruler, optical length tape scale encoder device, linear transducer means (LVDT), interferometry, etc.).

Sediment core sample 26 may comprise a real-world sample of actual sediments taken directly from the bottom of a lake, river, etc. Alternatively, sediment core sample 26 may be artificially prepared in the laboratory, by placing mixtures of water and particles into coring tube 30 and allowing the mixture to settle and consolidate for a sufficient period of time (e.g., 1–100 days).

Piston/cylinder means 16, 18 attached to the ends of channel 12 drive the non-uniform flow. The sediment test section in the channel experiences the equivalent of one piston stroke volume 40, 41 across its surface with each piston stroke. The cross-sectional area of the piston arrangement may be approximately 500 cm$^2$ and that of the channel may be approximately 20 cm$^2$. The velocity in channel 12 from the oscillating piston is calculated from conservation of mass principles:

$$A_p V_p = A_c V_c, \qquad (3)$$

$A_p$=cross-sectional area of piston (m$^2$),
$A_c$=cross-sectional area of channel (m$^2$),
$V_p$=velocity of piston(s) (m/s),
$V_c$=channel velocity (m/s).
This yields, $$V_c = 25 V_p, \qquad (4)$$

when $A_p/A_c=25$.

Figure 4:
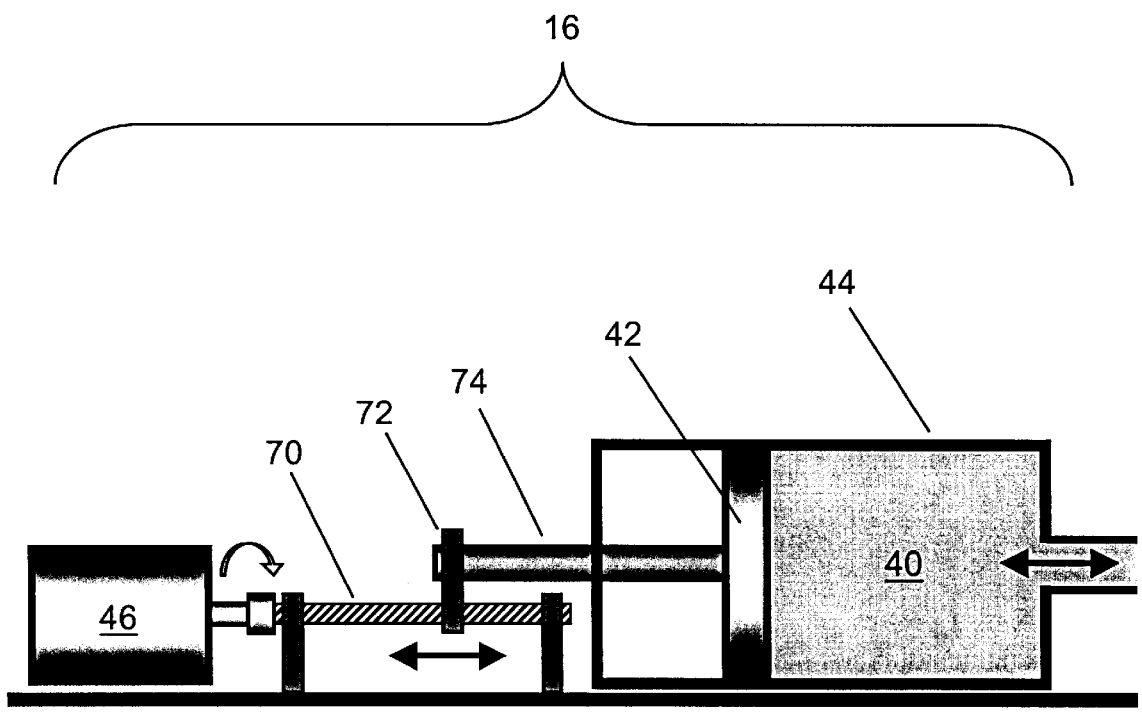
FIG. 4 shows a schematic elevation view of an example of a piston/cylinder drive mechanism for forcing oscillatory flow, according to the present invention.

FIG. 4 shows a schematic elevation view of an example of a piston/cylinder drive mechanism 16 for forcing non-uniform flow, according to the present invention. Piston 42 is housed inside of cylinder 44, and pushes or pulls water (or other fluid) contained within volume 40. Stepper motor 46 rotates a linear ball-screw 70 forwards or backwards, which, in turn, drives piston rod 74 via linkage 72. Stepper motor 46 may make 200 steps per revolution (1.8° per step). The maximum torque produced by the motor is 1,100 in-oz and occurs between 100–1,500 step/s. Above 1,500 step/s, the torque decreases rapidly and the motor tends to stall. Ball-screw 70 may provide 1-inch linear travel for every 4 revolutions. Therefore, with this combination of design parameters, the largest stable velocity created by the pistons may be approximately 1.2 m/s.

Stepper motor 46 may be computer controlled using the SMC40 Intelligent Indexer Version 1.13 software developed by Anaheim Automation, Inc. A simple program for the controller is a trapezoidal "move" comprising a constant piston acceleration period, a constant rate period, and a constant deceleration period (returning to zero velocity). Dividing the trapezoid into equal sections of acceleration, constant rate, and deceleration yields a reasonable approximation to a half-sine wave.

Figure 5:
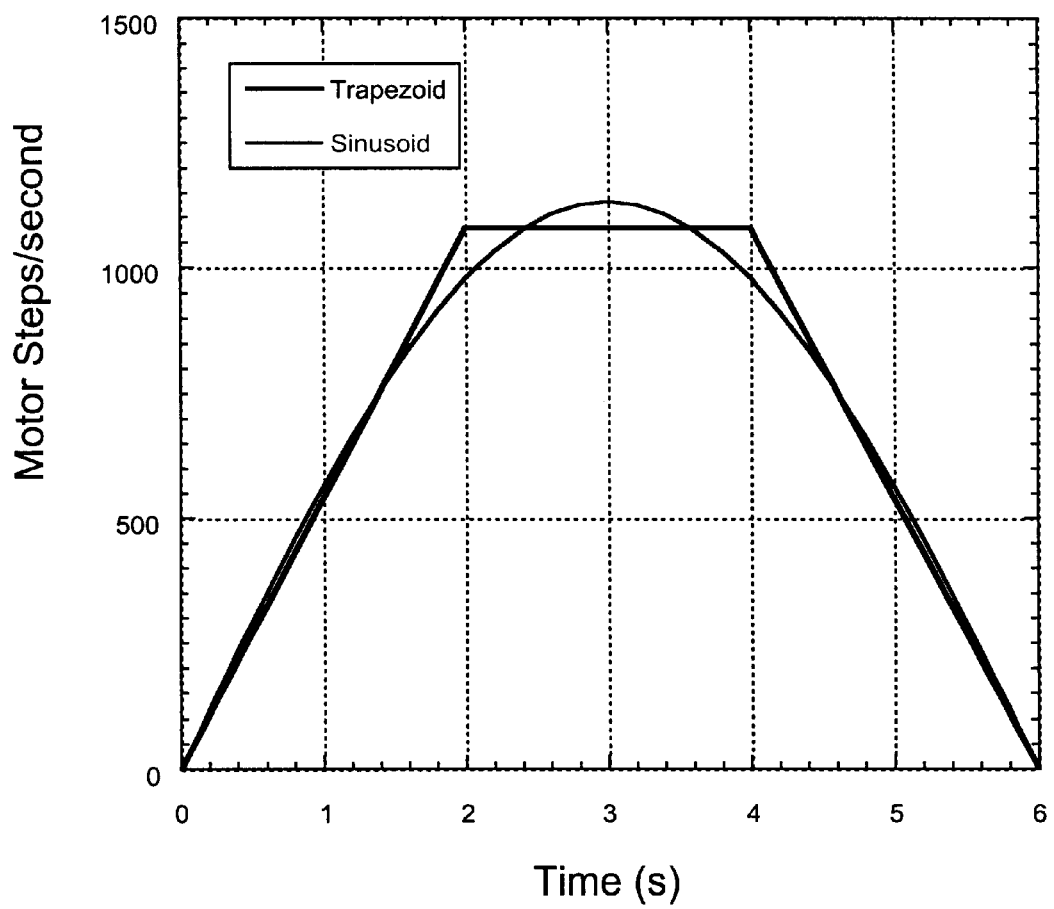
FIG. 5 shows an example of a stepper motor profile that closely approximates a half-sine wave, according to the present invention.

FIG. 5 shows an example of a stepper motor profile that closely approximates a sine wave, according to the present invention. Shown are half-periods of the motor movement necessary to yield a 27.5 gpm peak flow rate for a sinusoidal and a trapezoidal wave shape. The configuration for the trapezoidal move can be scaled for any motor rate and corresponding flow rate to simulate multiple wave conditions. More complex waveforms could also be simulated by using multi-step acceleration and deceleration periods in the controller program.

When the two piston/cylinder mechanisms are operated 180° out of phase they aid each other (one piston is pushing and the other is pulling) and provide a preferential pathway for the flow through the channel and test section, rather than forcing flow into Tank A or C. Therefore, the velocity over the test section (between the two pistons) is:

$$V_{testsection} = V_c \qquad (5)$$

Piston velocities may be controlled by the stepper motor, and can range from 0 to 0.048 m/s. Therefore, oscillating velocities in the test section with no superimposed unidirectional current may be between −1.2 and 1.2 m/s.

A constant, superimposed, unidirectional current may be generated when the head difference between Tanks A (56) and C (60) is kept constant. The oscillatory forcing by the pistons does not affect the forcing of the superimposed unidirectional current because Tank A (56) and C (60) are open to the atmosphere and are always free to spill excess water into the central reservoir of Tank B (58). In an alternative design that doesn't use open tanks (i.e., unpressurized tanks), a unidirectional pump-driven current would not allow a reversal of flow direction (for oscillatory flow), or maintain a constant unidirectional forcing, because the pump performance is dependent on the downstream head (pressure). Ultimately, a constant, superimposed unidirectional flow can only be maintained by constant Δh achieved by the example shown in FIG. 3. Experimentally, we have found that the three-tank arrangement illustrated in FIG. 3 produces very stable unidirectional flow.

In general, oscillatory flow regimes are never fully developed because of their transient nature. Furthermore, shear stresses are higher than those predicted by the fully developed assumptions, due to the larger velocity gradient in the boundary layer during developing flows. Because the oscillatory flow is also time dependent, numerical modeling may be used to determine the shear stress time history. The model for calculating shear stress will be discussed later. Maximum shear stress for the associated undeveloped oscillatory flow conditions (1.2 m/s) in SEAWOLF is approximately 10 Pa.

The SEAWOLF apparatus can simulate a wide variety of wave shapes, amplitudes, and periods. A commonly used waveform is a sinusoidal wave. For sinusoidal motion a piston mechanism 16, 18, the piston velocity is given by:

$$V_p(t) = \frac{L\pi}{T}\sin(\omega t), \quad (6)$$

where: L=stroke length (up to 0.4 m),
T=wave period (s),
ω=angular velocity (2π/T) (radians/s),
t=time (s).
This yields a sinusoidally varying flow velocity over the test section of $$V_c = \frac{L\pi}{T}\left(\frac{A_p}{A_c}\right)\sin(\omega t), \quad (7)$$

The amplitude of the wave and maximum piston velocity, $V_p$, is $L\pi/T$ for equation (6). Since the maximum piston velocity, $V_p$, is 0.048 m/s ($V_c$=1.2 m/s), the associated maximum wave period, T, for a 0.4 m maximum stroke length, L, is 26 s (in this example).

By using linear wave theory, an estimate can be made of the horizontal, bottom orbital velocities of a wave for a given wave height, wave period, and water depth. Given a range of wave periods from 3–25 seconds and a range of wave height between 0.5 and 10 m, the water depth for which the bottom orbital velocity is equal to the limiting oscillatory velocity produced by the piston and motor configuration illustrated in FIG. 4 can be determined.

Figure 6:
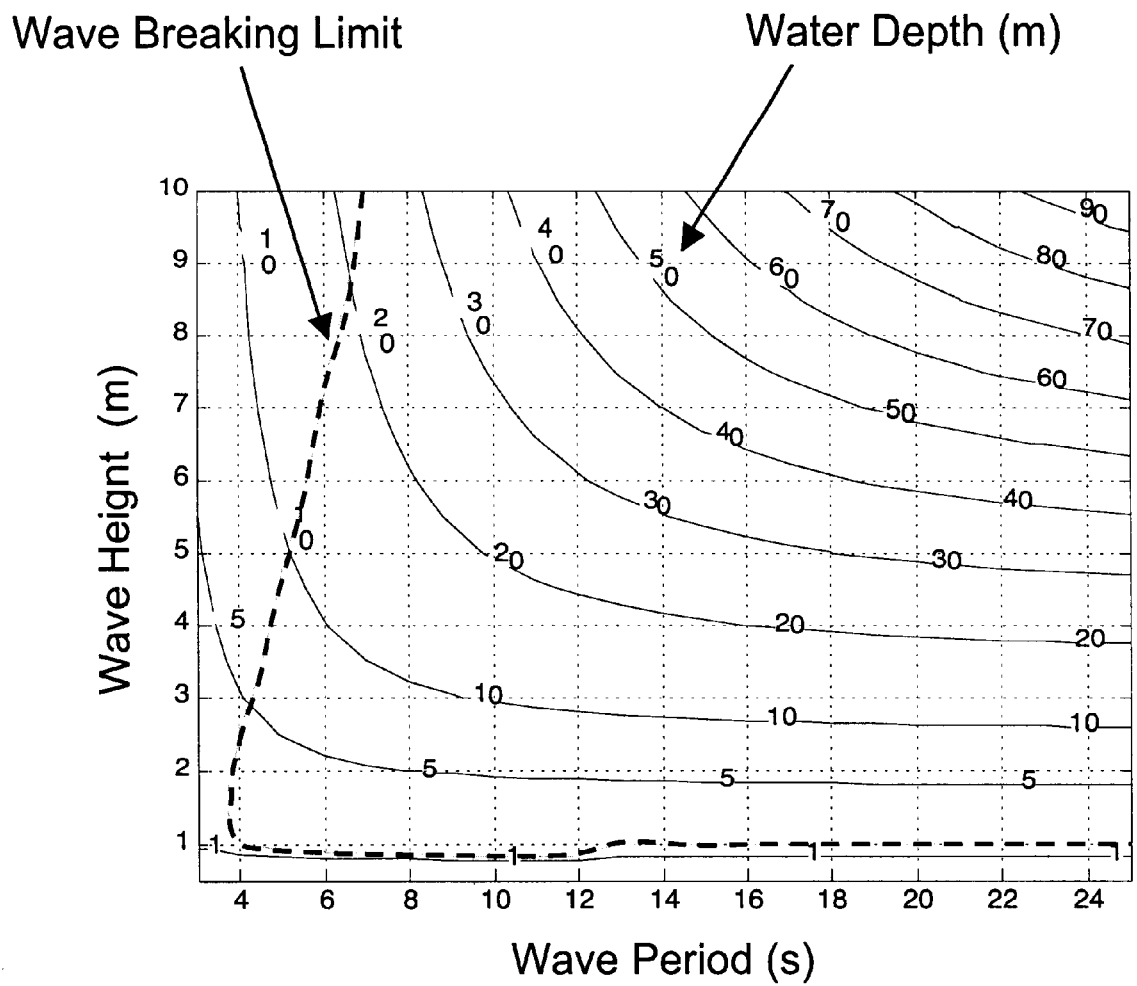
FIG. 6 shows the limiting (i.e., minimum) water depth that bottom orbital velocities can be produced by the apparatus shown in FIG. 3, as a function of wave height and wave period.

FIG. 6 shows the limiting (minimum) water depth that bottom orbital velocities can be produced by the apparatus shown in FIGS. 3 and 4 as a function of wave height and wave period. FIG. 6 assumes a maximum channel oscillatory velocity of 1.2 m/s. FIG. 6 provides limits of wave height, wave period, and water depth that a SEAWOLF flume can simulate within a particular set of operational limits of the motor drive and piston stroke length (e.g., $V_c$=1.2 m/s). Contour lines are of water depth in meters. The dashed line indicates a wave-breaking limit. Conditions below and to the left of the dashed line represent unstable wave conditions that will break.

Because the bottom boundary layer in a 2 cm deep flume/channel will be different from a free surface, the shear stresses produced in the flume will not be identical to the shear stresses produced by the surface wave and associated bottom orbital velocities. However the results shown in FIG. 6 can be considered a reasonable first-order estimate of the limits on wave conditions that a SEAWOLF apparatus can simulate.

Flow Tests

Several experiments were conducted in the SEAWOLF oscillatory flume to validate design parameters and test equipment. A DeltaForce™ magnetic flow meter attached directly to one end of the channel was used to provide real-time measurements of flow conditions. Wave shape variations with peak flow rates of 40 gpm were studied.

Several flow conditions were tested where motor speeds and valve configurations were altered. All motor movements were trapezoidal approximations of a half sine wave. Tests were preformed for both valves fully open and valves completely closed conditions. The tests demonstrate that the each motor-piston movement closely simulates sinusoidal flow rates and velocities under both valve open and valve closed conditions. In some cases, there appeared to be slightly lower velocities in the first quarter (acceleration) of the wave cycle compared to the second quarter (deceleration). This may have been due to the smaller diameter pipe (1.5 in.) in the flow meter attached at on end of the channel compared to the 2 in. diameter elsewhere in the system. The smaller diameter in the flow meter could cause more head loss during the accelerated flow compared to the decelerated flow. If further testing shows this effect to be significant and consistent, it could be corrected by using a valve on the opposite side of the channel to equilibrate any head loss associated with the flow meter. In addition, once the flow meter is used to establish flow characteristics for specific piston motions and tank configurations, it could be removed.

Valve closed cases generate 5–10 gpm greater peak flow rates compared to valve open cases under identical motor-piston movements for the conditions tested. This indicates that the flow impulse is significantly redirected to the open tanks when the valves are open, although the oscillatory flow in the valve-open case remains sinusoidal. When the valves are closed, the flow cannot be redirected to the tanks and must travel through the flume channel. Flow meter measurements for the valve-closed cases are consistent with calculations for the volume of fluid displaced by the piston movement.

Figure 7:
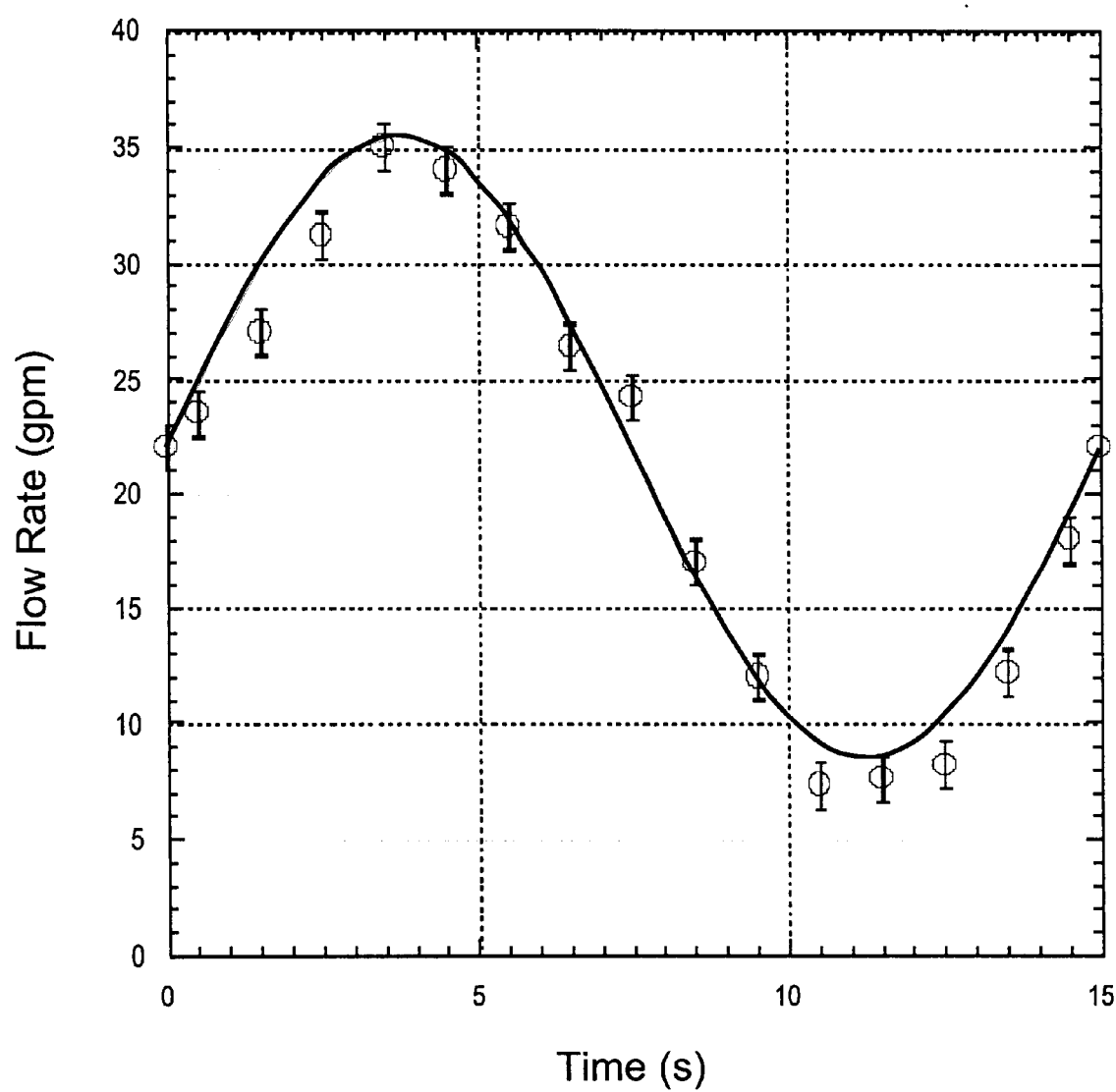
FIG. 7 shows a plot of flow rate (gpm) as a function of time (seconds), with superimposed unidirectional flow, according to the present invention.

Additional testing was performed for combined oscillatory and unidirectional flow. FIG. 7 shows a plot of flow rate (gpm) as a function of time (seconds), with superimposed unidirectional flow, according to the present invention. FIG. 7 shows the results for a 22 gpm unidirectional flow (Δh=0.3 m for valve open case) superimposed upon a 15 gpm peak, sinusoidal, 15 s period oscillating flow. Experimental measurements correlate well with numerical modeling. Measurements indicate that the sinusoidal oscillatory flow generated by the pistons was maintained in the presence of the unidirectional flow. The maximum flow rate was 36 gpm (approximately 22 gpm+15 gpm) and the minimum flow rate was 8 gpm (approximately 22 gpm−15 gpm).

Erosion Tests

Erosion tests were performed on a 310 μm quartz sand that has been previously tested extensively in a unidirectional SEDFlume. Tests were performed with the valves open for the piston moves generating pure oscillatory motion with no superimposed unidirectional flow. Table 1 shows the SEAWOLF experimental results for these piston moves. Erosion rate is measured as the operator controls upward movement of the core over the duration of the experiment. It should be noted that erosion rates measured in SEDFlume are consistent with known erosion rates for sands under multiple shear stress and grain size conditions.

TABLE 1

Erosion for 310 μm quartz sand

| Average Flow (gpm) | Maximum Flow (gpm) | Erosion Rate (cm/s) | Effective Shear Stress for Wave (Pa) |
|---|---|---|---|
| 3.27 | 6.0 | ~0 | — |
| 9.3 | 15.0 | 0.006 | 0.7 |
| 12.0 | 18.3 | 0.0183 | 1.0 |
| 13.7 | 22.0 | 0.05 | 1.5 |

The equation describing the erosion rate as a function of shear stress is:

$$E = A\rho^m \tau^n \quad (8)$$

where $A=1.7\times10^{-2}$, m=0, and n=2.7 for 310 μm quartz. Solving equation (8) for shear stress, τ, and substituting the values in Table 1 for erosion rate, E, yields an effective shear stress for the wave motion. Effective shear stress in Table 1 is the shear stress from the unidirectional SEDFlume that induces the same erosion rate in SEAWOLF.

Experiments were also performed with sediments from the Canaveral Ocean Dredged Material Disposal Site for the combined unidirectional and oscillatory flow case shown in FIG. 7. The sediments were 63% sand and 37% silt with a median grain size of 92 $\mu$m. The constants derived from the unidirectional tests for equation (8) are $A=1.22\times10^{10}$, $m=-66.8$, and $n=2.71$. The erosion rate measured for the superimposed oscillatory and linear flow conditions of FIG. 7 and Table 1, Case 2 was 0.00133 cm/s. With this erosion rate, equation (8) yields an effective shear stress of 2.4 Pa. The shear stress in SEAWOLF for a 22 gpm unidirectional, fully developed flow rate is approximately 1.4 Pa (Table 1). Clearly, undeveloped oscillatory flows generate significantly higher erosion rates and effective shear stresses than the equivalent unidirectional, fully developed flow rates. The effective shear stress is higher for the oscillatory case because (1) either the flow is not fully developed, (2) the maximum flow (37 gpm) and related shear stress (~4.7 Pa from modeling results) is the controlling factor, or (3) oscillatory flow may weaken the sediment surface more than a constant, unidirectional flow.

The effective shear stress for unsteady wave/current conditions may be used to represent an equivalent erosion rate for a unidirectional, fully developed flow. Erosion rate is generally a function of shear stress to a power greater than one ($E \sim \tau^{>1}$). It is also probable that a portion of the wave period may include shear stress less than the critical shear stress for initiation of erosion. Therefore, effective shear stress is not the same as average shear stress or maximum shear stress for the wave/current condition, but a function of shear stress time history and critical shear stress. Nevertheless, effective shear stress is a useful description for bulk erosion measurements because it is operationally impossible to measure cohesive sediment erosion rates for small time periods within a wave period. The effective shear stress is also the simplest and most useful measurement for model input. To determine shear stresses at discrete times within the wave period requires intense numerical computations that are beyond the capacity of most large domain sediment transport models.

Extensive libraries of sediments exist in which the constants for equation (8) have been determined under unidirectional flow. A general relationship between various waveforms and effective shear stresses could be developed through further experiments with more quartz sands and other natural sediments with well known erosion properties for unidirectional, fully developed flow. These experiments coupled with modeling efforts, would create a much-improved understanding of erosion processes of combined wave and current regimes.

At present, effective shear stress can only be calculated for sediments with known unidirectional, fully developed flow generated erosion rates. Effective shear stress is also specific to both sediment properties and wave/current conditions. Additional SEAWOLF erosion tests and modeling can be performed to develop relationships that describe the influence of wave/current conditions on effective shear stress.

The particular examples discussed above are cited to illustrate particular embodiments of the invention. Other applications and embodiments of the apparatus and method of the present invention will become evident to those skilled in the art. In particular, more than two piston/cylinder mechanisms may be used in parallel to provide enhanced capability to generate complex waveforms.

The actual scope of the invention is defined by the claims appended hereto.

What is claimed is:

1. An apparatus for eroding sediments from a sediment core sample, comprising:
   a flow channel for conveying a flowing stream of water, the channel having a bottom surface, an entrance and an exit;
   erosion means, attached to an opening in the bottom surface of the flow channel, for exposing a sediment core sample to the flowing stream of water, whereby sediments are eroded and introduced into the flow stream; and
   means for forcing a unidirectional flow of water through the channel, comprising:
      a first open storage tank;
      a second open storage tank;
      a third open storage tank;
      a pump configured to pump water from the first second tank into the first tank;
      upstream piping means for conveying water from the first tank to the entrance of the flow channel; and
      downstream piping means for conveying water from the exit of the flow channel to the third tank;
      wherein the first tank is configured so that water overflowing from the first tank spills into the second tank;
      wherein the third tank is configured so that water overflowing from the third tank spills into the second tank; and
      wherein the first tank is configured so that water that spills into the second tank is at a higher height than the water that spills from the third tank into the second tank;
      whereby the pressure created by the difference in water heights between the first and third tanks drives the unidirectional flow of water through the flow channel.

2. The apparatus of claim 1, wherein the first tank comprises a movable gate with an adjustable height, wherein the gate controls the height at which water spills from the first tank into the second tank.

3. The apparatus of claim 1, wherein the upstream piping means comprises an upstream flow control valve.

4. The apparatus of claim 1, wherein the downstream piping means comprises a downstream flow control valve.

5. The apparatus of claim 1, further comprising means for measuring the flow rate of water flowing through the flow channel.

6. The apparatus of claim 1, further comprising one or more sediment traps, attached to the bottom of the flow channel and located downstream of the erosion means, for gravitationally separating and capturing bedload sediments eroded and transported by the flow stream.

7. An apparatus for eroding sediments from a sediment core sample, comprising:
   a flow channel for conveying a flowing stream of water, the channel having a bottom surface, an entrance and an exit;
   erosion means, attached to an opening in the bottom surface of the flow channel, for exposing a sediment core sample to the flowing stream of water, whereby sediments are eroded and introduced into the flow stream;
   means for forcing a non-uniform flow of water through the channel; and
   means for forcing a unidirectional flow of water through the channel, comprising;

a first open storage tank;
a second open storage tank;
a third open storage tank;
a pump configured to pump water from the second tank into the first tank;
upstream piping means for conveying water from the first tank to the entrance of the flow channel; and
downstream piping means for conveying water from the exit of the flow channel to the third tank;
wherein the first tank is configured so that water overflowing from the first tank spills into the second tank;
wherein the third tank is configured so that water overflowing from the third tank spills into the second tank; and
wherein the first tank is configured so that water that spills into the second tank is at a higher height than the water that spills from the third tank into the second tank;
whereby the pressure created by the difference in water heights between the first and third tanks drives the unidirectional flow of water through the flow channel.

8. The apparatus of claim 7, wherein said means for forcing a non-uniform flow comprises a first piston/cylinder mechanism attached to the entrance of the flow channel and a second piston/cylinder mechanism attached to the exit of the flow channel.

* * * * *